United States Patent [19]

Tsuei et al.

[11] Patent Number: 5,433,953
[45] Date of Patent: Jul. 18, 1995

[54] MICROCAPSULES AND METHODS FOR MAKING SAME

[75] Inventors: Alexander C. Tsuei, Woodbury; Smarajit Mitra, West St. Paul, both of Minn.

[73] Assignee: Minnesota Mining and Manufacturing, St. Paul, Minn.

[21] Appl. No.: 179,611

[22] Filed: Jan. 10, 1994

[51] Int. Cl.$^6$ .......................... A61K 9/50; A61K 31/14
[52] U.S. Cl. ................................. 424/489; 428/402.21; 428/402.2; 264/4.1; 264/4.33; 264/4.7
[58] Field of Search ................. 424/489; 264/4.1, 4.33, 264/4.7; 428/402.21, 402.2

[56] References Cited

U.S. PATENT DOCUMENTS

| | | | |
|---|---|---|---|
| 3,464,926 | 9/1969 | Vandegaer et al. | 252/316 |
| 3,516,941 | 6/1970 | Matson | 252/316 |
| 3,522,346 | 7/1970 | Chang | 424/35 |
| 3,575,882 | 4/1971 | Vandegaer | 252/316 |
| 3,577,515 | 4/1971 | Vandegaer | 424/32 |
| 3,645,911 | 2/1972 | van Besauw et al. | 252/316 |
| 3,860,565 | 1/1975 | Barber, Jr. | 260/77.5 |
| 4,056,610 | 11/1977 | Barber, Jr. et al. | 424/32 |
| 4,138,362 | 2/1979 | Vassiliades et al. | 252/316 |
| 4,756,906 | 7/1988 | Sweeny | 424/63 |
| 5,169,632 | 12/1992 | Duell et al. | 424/408 |
| 5,204,184 | 4/1993 | Shields et al. | 428/402.21 |

FOREIGN PATENT DOCUMENTS

| 576377 | 12/1993 | European Pat. Off. . |
|---|---|---|
| 93/00160 | 1/1993 | WIPO . |

OTHER PUBLICATIONS

P. D. Deasey, Microencapsulation and Related Drug Processes, Marcell Dekker, Inc., (1984).

McGinity et al., Influences of Matrixes on Nylon-Encapsulated Pharmaceuticals, Journal of Pharmaceutical Sciences, vol. 70, No. 4, Apr. (1981).

*Primary Examiner*—Thurman K. Page
*Assistant Examiner*—James M. Spear
*Attorney, Agent, or Firm*—Gary L. Griswold; Walt N. Kirn; Dale A. Bjorkman

[57] ABSTRACT

A method for microencapsulating quaternary ammonium salts by interfacial polymerization. The polar component comprises a quaternary ammonium salt, glycerine, triethyleneglycol diamine, a C 4–10 straight or branched aliphatic compound having two primary amine functionalities, and a C 4–10 straight or branched aliphatic compound having at least three primary amine functionalities. The glycerine-immiscible oil component comprises mineral oil, an aliphatic polyisocyanate and a surfactant. The mole equivalent ratios of primary amine to isocyanate in this reaction is about 0.01–3:1. Microcapsules made by this method are unique and provide surprising benefits in durability, elasticity and barrier properties in resistance to leaching of the microcapsule fill material.

16 Claims, No Drawings

MICROCAPSULES AND METHODS FOR MAKING SAME

FIELD OF THE INVENTION

This invention relates to microcapsules made by an interfacial polymerization reaction. More specifically, this invention relates to microcapsule having quaternary ammonium salts in the fill of said microcapsule.

BACKGROUND OF THE INVENTION

Microencapsulation is the envelopment of small, solid particles, liquid droplets, or gas bubbles with a coating, usually a continuous coating. Many terms are used to describe the contents of a microcapsule such as active agent, active core, core material, fill, internal phase, nucleus, and payload. The coating material used to form the outer surface of the microcapsule is called a coating membrane, shell, or wall. It may be an organic polymer hydrocolloid, sugar, wax, metal, or inorganic oxide. Microcapsules usually fall in the size range of between 1 and 2000 microns, although smaller and larger sizes are known.

In interfacial polymerization reactions, the fill is typically a liquid rather than a solid. Interfacial polymerization involves the reaction of various monomers at the interface between two immiscible liquid phases to form a film of polymer that encapsulates the disperse phase. The monomers diffuse together and rapidly polymerize at the interface of the two phases to form a thin coating. The degree of polymerization can be controlled by the reactivity of the monomers chosen, their concentration, the composition of either phase vehicle, and by the temperature of the system.

Microcapsules produced through interfacial polymerization having shell walls composed of polyamides, polyureas, polyurethanes, and polyesters are known; see U.S. Pat. Nos. 3,516,941, 3,860,565, 4,056,610, and 4,756,906. In some instances the shell walls of these conventional microcapsules are very porous and consequently relinquish their fill too rapidly for some applications. Therefore, the microcapsules may have to be post-crosslinked with such crosslinking agents as polyfunctional aziridines. The crosslinking provides shell walls with greater structural integrity and reduced porosity. Of course, an obvious disadvantage to post-crosslinking of curing is that it adds another step the microcapsule production process.

SUMMARY OF THE INVENTION

The present invention provides a method for microencapsulating quaternary ammonium salts by interfacial polymerization. A polar component is admixed with a glycerine-immiscible oil component under conditions effective to form a polar liquid-in-oil emulsion, so that the polar component is dispersed in the form of microscopic emulsion droplets in a glycerine-immiscible oil component continuous phase. Each of these droplets is therefore surrounded with a solid capsule wall. The polar component comprises a quaternary ammonium salt, glycerine, triethyleneglycol diamine, a C 4-10 straight or branched aliphatic compound having two primary amine functionalities, and a C 4-10 straight or branched aliphatic compound having at least three primary amine functionalities. The compound having at least three primary amines may optionally be interrupted with one or more non-contiguous heteroatoms selected from the group consisting of O, NR, S and P, wherein R is selected from H and a C1-10 aliphatic moiety. The glycerine-immiscible oil component comprises mineral oil, an aliphatic polyisocyanate and a surfactant. The mole equivalent ratios of primary amine to isocyanate in this reaction is about 0.01-3:1.

Microcapsules made by this method are unique and provide surprising benefits in durability, elasticity and barrier properties in resistance to leaching of the microcapsule fill material.

DETAILED DESCRIPTION

Quaternary ammonium salt compounds have been found to be particularly advantageous for use in fighting viral infections such as AIDS, hepatitis and the like. It would be desirable to incorporate such compounds in a latex matrix such as a surgical glove or laminar sheet for infection control purposes. If the glove or sheet is breached by a scalpel, needle or the like, or if the material simply tears for one reason or another, immediate delivery of an antiviral agent at the site could provide important immediate treatment with prevention of disease.

Quaternary ammonium salts are generally not appropriate for direct incorporation in latex articles because they may interfere with the preparation and/or storage of emulsion and latex products due to the strong surface activity of these compounds. Further, it is questionable whether compounds dispersed as such throughout a latex matrix will be properly delivered to the site of breach of the latex article, because the compounds would not be available in sufficient quantity to flow out of the latex matrix.

It is particularly desired to provide microcapsules containing quaternary ammonium salts for incorporation in latex articles used in infection control, and such incorporation has been previously suggested. However, it is very difficult to encapsulate such compounds by a liquid-liquid process because the quaternary ammonium salts tend to accumulate at the interfacial regions in any oil/water dispersion and are difficult to capture within shell walls. Effective encapsulation of aqueous solutions of quaternary ammonium salts remains a technical challenge.

Effective microcapsules containing quaternary ammonium salts for incorporation in latex articles must both survive the process of placing the microcapsules in the latex matrix, and must exhibit good barrier properties so that the fill material is not leached out from the microcapsule and lost over time. These microcapsules additionally must have sufficient elasticity so that a sharp object that would pierce the latex matrix does not displace the microcapsule, but rather slices through or punctures the microcapsule.

It has surprisingly been found that microcapsules suitable for incorporation into latex structures used for infection control purposes and incorporating quaternary ammonium salts may be made by a unique combination of a carefully selected combination of reactive amines and isocyanates that are reacted in specific solvents, together with a surfactant in the mineral oil of the reaction system. This unique combination of shell wall components and reaction environment enables the preparation of microcapsules having surprising properties of durability, elasticity and barrier to leaching.

The general conditions and requirements for producing microcapsules through interfacial polymerization reactions are known. See, for example, P. D. Deasy, Microcapsulation and Related Drug Processes, Marcell Dekker, Inc., (1984). Through the unique selection of various elements of known interfacial reactions, the surprising results provided herein are achieved.

Quaternary ammonium salts useful for incorporation in microcapsules of the present invention include the specialty biocides such as alkyl dimethyl benzyl and dialkyl dimethyl ammonium chloride, methylbenzethonium chloride, and chlorhexidine gluconate and mixtures thereof. Such compounds and specialty biocides are commercially available in various formulations, for example, from Lonza Inc., under the trade names Bardac ®, Barquat ®, Hyamine ®, and Spectradyne ®. Other quaternary ammonium compounds include quaternaries for non-biocidal applications, such as stearyl dimethyl benzyl ammonium chloride, cetyl trimethyl ammonium chloride and dicetyl dimethyl ammonium chloride, alkyl imidaxolinium Methosulfate, commercially available from Lonza, Inc. under the name Carsosoft ® and Carsoquat ®.

Amine functionalities are provided by three different sources in the inventive method. The first source is triethylene glycol diamine.

The second source of amine functionality is a C 4–10 straight or branched aliphatic compound having two primary amine functionalities, or mixtures thereof.

More preferably, the di-primary amine is a C2–C8 alkyl diamine having no less than two carbons between the amine functionalities.

Examples of preferred aliphatic diamines include 1,2-diaminoethane; 1,3-diaminopropane; 1,2-diaminopropane; 1,3-diamino-2-hydroxypropane; 1,4-diaminobutane; 1,3-diaminobutane; 1,5-diaminopentane; 1,3-diaminopentane; 1,6-diamino-n-hexane; 2-methylpentamethylenediamine; 1,7-diaminoheptane; 1,8-diaminooctane; 1,9-diaminononane; 1,10-diaminodecane; 1,12-diaminododecane; diaminocyclohexanes; bis(4-aminocylcohexyl)methane and 1,8-diamino-p-menthane.

The third source of amine functionality is a C 4–10 straight or branched aliphatic compound having at least three primary amine functionalities. This compound may optionally be interrupted with one or more non-contiguous heteroatoms selected from the group consisting of O, NR, S and P, wherein R is selected from H and a C1–10 aliphatic moiety. It is permissible for this third source also to be provided by mixtures of compounds meeting this definition.

More preferably, the third amine source is a C6–C9 alkyl triamine having no less than two carbons between the amine functionalities. Examples of preferred aliphatic triamines include tris(2-aminoethyl)amine, (tris)amino-1,6 hexamethylene biuret adduct and N,N'-di(6-aminohexyl)-(6-aminohexylamino)succinamide and polyoxypropyleneamines, commercially available as Jeffamine T series amines from Texaco Chemical Co.

The aliphatic polyisocyanates used in the present method may optionally be selected from aliphatic polyisocyanates containing two isocyanate functionalities, three isocyanate functionalities, or more than three isocyanate functionalities, or mixtures of these polyisocyanates. Preferably, the aliphatic polyisocyanate contains 5–30 carbons. More preferably, the aliphatic polyisocyanate comprise one or more cycloalkyl moieties. Examples of preferred isocyanates include dicyclohexylmethane-4,4'-diisocyanate; hexamethylene 1,6-diisocyanate; isophorone diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato)cyclohexane; biuret of hexamethylene diisocyanate; urea of hexamethylene diisocyanate; trimethylenediisocyanate; propylene-1,2-diisocyanate; and butylene-1,2-diisocyanate.

The mole equivalent ratio of total primary amine functionality to isocyanate functionality in the system is preferably about 0.8:1 to 1:1.2, and more preferably about 1:1.1.

The surfactant is selected from nonionic surfactants. Examples of such surfactants include polyether block copolymers, such as Pluronic TM and Tetronic TM, polyoxyethylene adducts of fatty alcohols, such as Brij TM surfactants, and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as Arlacel C ® surfactants.

It is surprising that the present reaction allows formation of microcapsules having the desired properties, wherein the microcapsules have at least about 5% by weight of quaternary ammonium salt in the microcapsule.

Preferably, the reaction solution contains no more than a small amount of water. It has been found that the presence of large amounts of water in the polar component of the reaction solution negatively affects the barrier properties of the resultant shell. Preferably, the polar component of the reaction solution contains no more than about 20% of water by weight. More preferably, no more than about 10%, and most preferably no more than about 5% water in the polar component.

In a particularly preferred embodiment, the interfacial polymerization is carried out by admixing
a) a polar component comprising
  i) a quaternary ammonium salt
  ii) glycerine
  iii) triethyleneglycol diamine
  iv) $H_2NCH_2(CH_3)CHCH_2CH_2CH_2NH_2$
  v) $N(CH_2CH_2NH_2)_3$
b) a glycerine-immiscible oil component comprising
  vi) mineral oil
  vii) $OCN(C_6H_{10})CH_2(C_6H_{10})NCO$
  viii) a surfactant;

wherein each of ingredients iii), iv) and v) are present at mole equivalent ratios of primary amine to isocyanate of about 0.2–0.5:1. This admixing is conducted under conditions effective to form a polar liquid-in-oil emulsion, wherein said polar component is dispersed in the form of microscopic emulsion droplets in a glycerine-immiscible oil component continuous phase, and thereby surrounding each of said droplets with a solid capsule wall.

The following non-limiting examples further illustrate the present invention.

EXAMPLES

Example 1

A solution was made of 90 grams of 2-methylpentamethylenediamine (Dytek A amine, Du Pont Chemicals, Wilmington, Del.), 82 grams of triethylene glycol diamine (Jeffamine ® EDR-148, Texaco Chemical Co., Houston, Tex.), 62 grams of tris(2-aminoethyl)amine (Aldrich Chemical Co., Inc., Milwaukee, Wis.), and 82 grams of Bardac-2270E in 470 grams of glycerol at room temperature. The resulting solution was added to a stirred solution of 3.5 liters mineral oil with 0.17 weight percent Arlacel® C, in a two-gallon baffled reactor, using a 3-bladed Mixco-A310 turbine stirrer (390 rpm, 3.8 inches dia.). The emulsion formed was stirred at 390 rpm for 10 min. in a 15° C. water bath. To this mixture was added a total of 562 grams of dicyclohexylmethane-4,4'-diisocyanate (Desmodur W, Miles Inc., Pittsburgh, Pa.) in 0.8 liter of mineral oil over 10 minutes, then the bath temperature was raised to 63° C. for 40 minutes. The mixture was stirred for 18 hours, allowed to cool to room temperature and the microcapsules were collected and rinsed with hexane or heptane. The capsules were then sieved to give the desired size microcapsules.

The resulting microcapsules were flexible, had a fairly strong shell and were substantially leach proof.

Example 2

A solution was made of three grams of 1,3-diaminopropane (Aldrich Chemical Co., Inc., Milwaukee, Wis.), 4.3 grams of triethylene glycol diamine (Jeffamine® EDR-148, Texaco Chemical Co., Houston, Tex.), 5 grams of tris(2-aminoethyl)amine (Aldrich Chemical Co., Inc., Milwaukee, Wis.), and 4.1 grams of Bardac-2270E in 23.4 grams of glycerol at room temperature. The resulting solution was added to a stirred solution of 200 ml mineral oil with 0.17 weight percent Arlacel® C, in a one-liter baffled reactor, using a 6-bladed FBT-Rushton turbine stirrer (230 rpm, 5.0 cm dia.). The emulsion formed was stirred at 230 rpm for 10 min. in a 15° C. water bath. To this mixture was added a total of 32 grams of dicyclohexylmethane-4,4'-diisocyanate (Desmodur W, Miles Inc., Pittsburgh, Pa.) in 60 ml of mineral oil over 10 minutes, then the bath temperature was raised to 63° C. for 40 minutes. The mixture was stirred for 18 hours, allowed to cool to room temperature and the microcapsules were collected and rinsed with hexane or heptane. The capsules were then sieved to give the desired size microcapsules.

Comparative Example 1

A solution was made of 160 grams of 1,3-diaminopropane (Aldrich Chemical Co. Inc., Milwaukee, Wis.), 16 grams of triethylene glycol diamine (Jeffamine® EDR-148, Texaco Chemical Co., Houston, Tex.), 80 grams of triethylenetetramine (Texaco Chemical Co., Houston, Tex.), and 90 grams of Bardac-2270E in 470 grams of glycerol at room temperature. The resulting solution was added to a stirred solution of 5.1 liters mineral oil with 0.17 weight percent Arlacel® C, in a five-gallon baffled reactor, using a pair of 3-bladed Mixco-A310 turbine stirrer (150 rpm, 6.5 inches dia.). The emulsion formed was stirred at 150 rpm for 10 minutes in a 15° C. water bath. To this mixture was added a total of 540 grams of dicyclohexylmethane-4,4'-diisocyanate (Desmodur W, Miles Inc., Pittsburgh, Pa.) in 2.4 liters of mineral oil over 10 minutes, then the bath temperature was raised to 63° C. for 40 minutes. The mixture was stirred for 18 hours, allowed to cool to room temperature and the microcapsules were collected and rinsed with hexane or heptane. The capsules were then sieved to give the desired size microcapsules.

Comparative Example 2

A solution was made of 17.25 grams of polyoxyalkyleneamine (Jeffamine® D-230, Texaco Chemical Co., Houston, Tex.), 7.6 grams of polyoxypropyleneamine (Jeffamine® T-403, Texaco Chemical Co., Houston, Tex.), and 4 grams of Bardac-2270E (Lonza Chemical Co., Fair Lawn, N.J.) in 22.5 grams of glycerol at room temperature. The resulting solution was added to a stirred solution of 180 grams mineral oil with 0.17 weight percent Arlacel® C (ICI Americas Inc., Wilmington, Del.), in a one-liter baffled reactor, using a 6-bladed FBT-Rushton turbine stirrer (238 rpm, 5.0 cm dia.). The emulsion formed and stirred at 238 rpm for 10 min. in a 15° C. water bath. To this mixture was added a total of 15 grams of toluene diisocyanate (Du Pont Chemicals, Wilmington, Del.) in 100 grams of mineral oil over 10 mins, then the bath temperature was raised to 63° C. for 40 mins. The mixture was stirred for 18 hours, allowed to cool to room temperature and the microcapsules were collected and rinsed with hexane or heptane. The capsules were then sieved to give the desired size microcapsules.

Comparative Example 3

A solution was made of 11.9 grams of triethylene glycol diamine (Jeffamine® EDR-148, Texaco Chemical Co., Houston, Tex.) and 3 grams of tris(2-aminoethyl)amine, and 4.1 grams of Bardac-2270E in 22.5 grams of glycerol at room temperature. The resulting solution was added to a stirred solution of 200 ml mineral oil with 0.17 weight percent Arlacel® C, in a one-liter baffled reactor, using a 6-bladed FBT-Rushton turbine stirrer (235 rpm, 5.0 cm dia.). The emulsion formed was stirred at 235 rpm for 10 minutes in a 15° C. water bath. To this mixture was added a total of 26.4 grams of dicyclohexylmethane-4,4'-diisocyanate (Desmodur W, Miles Inc., Pittsburgh, Pa.) in 100 ml of mineral oil over 10 minutes, then the bath temperature was raised to 63° C. for 40 minutes. The mixture was stirred for 18 hours, allowed to cool to room temperature and the microcapsules were collected and rinsed with hexane or heptane. The capsules were then sieved to give the desired size microcapsules.

Comparative Example 4

Procedure same as Comparative Example 2. 8 grams of 1,3-diaminopropane, 4 grams of diethylenetriamine, and 36 grams of dicyclohexylmethane-4,4'-diisocyanate.

Comparative Example 5

Procedure same as Comparative Example 2. 5 grams of ethylenediamine, 4 grams of triethylene glycol diamine, 4.1 grams of triethylenetetraamine, and 15.1 grams of toluene diisocyanate.

Comparative Example 6

Procedure same as Comparative Example 2. 14.2 grams of 1,6-diaminohexane and 20 grams of toluene diisocyanate.

Comparative Example 7

Procedure same as Comparative Example 2. 26 grams of polyoxypropyleneamine (Jeffamine® T-403, Texaco Chemical Co., Houston, Tex.) and 13 grams of toluene diisocyanate.

Comparative Example 8

Procedure same as Comparative Example 2. 26 grams of polyoxyalkyleneamine (Jeffamine® D-230, Texaco Chemical Co., Houston, Tex.), 5 grams of triethylenetetraamine, and 20 grams of toluene diisocyanate.

Comparative Example 9

Procedure same as comparative Example 2. 6.4 grams of 2-methylpentamethylenediamine (Dytek A amine, Du Pont Chemicals, Wilmington, Del.), 1.7 grams of triethylenetetraamine, and 10 grams of toluene diisocyanate.

Comparative Example 10

Procedure same as Comparative Example 2. 8.3 grams of ethylenediamine, 3.6 grams of diethylenetriamine, and 15.1 grams of toluene diisocyanate.

It was found that the microcapsules made according to comparative examples 1, 4 and 7 had weak shells. Excessive leaching was found in the microcapsules made according to comparative examples 2, 8 and 9. Microcapsules made according to comparative examples 5, 6, 9, and 10 displayed brittleness. The microcapsules made according to comparative example 3 lost all of their fill immediately. These comparative examples showed that when one of the essential components was left out, i.e. the primary diamine, the primary triamine or the aliphatic polyisocyanate, the capsules made were inferior and did not provide the desired beneficial properties of elasticity, strength and/or resistance to leaching.

What is claimed is:

1. A method for microencapsulating quaternary ammonium salts by interfacial polymerization, which comprises admixing
    a) a polar component comprising
        i) a quaternary ammonium salt, or mixtures thereof;
        ii) glycerine
        iii) triethyleneglycol diamine
        iv) a C 4–10 straight or branched aliphatic compound having two primary amine functionalities selected from the group consisting of 1,2-diaminoethane; 1,3-diaminopropane; 1,2-diaminopropane; 1,3-diamino-2-hydroxypropane; 1,4-diaminobutane; 1,3-diaminobutane; 1,5-diaminopentane; 1,3-diaminopentane; 1,6-diamino-n-hexane; 2-methylpentamethylenediamine; 1,7-diaminoheptane; 1,8-diaminooctane; 1,9-diaminononane; 1,10-diaminodecane; 1,12-diaminododecane; diaminocyclohexanes; bis(4-aminocyclohexyl)methane; and 1,8-diamino-p-methane, or mixtures thereof;
        v) a C 4–10 straight or branched aliphatic compound having at least three primary amine functionalities, said compound selected from the group consisting of tris(2-aminoethyl)amine, (tris)amino-1,6 hexamethylene biuret adduct and N,N'-di(6-aminohexyl)-(6-aminohexylamino)-succinamide and polyoxypropyleneamine, or mixtures thereof; and
    b) a glycerine-immiscible oil component comprising
        vi) mineral oil
        vii) an aliphatic polyisocyanate that is soluble in the glycerine immiscible oil component, or mixtures thereof;
        viii) a surfactant, or mixtures thereof;
    wherein each of said ingredients iii), iv) and v) are present at mole equivalent ratios of primary amine to isocyanate of about 0.01–3:1;
    said admixing being conducted under conditions effective to form a polar liquid-in-oil emulsion, wherein said polar component is dispersed in the form of microscopic emulsion droplets in a glycerine-immiscible oil component continuous phase, and thereby surrounding each of said droplets with a solid capsule wall.

2. A method for microencapsulating quaternary ammonium salts by interfacial polymerization, which comprises admixing
    a) a polar component comprising
        i) a quaternary ammonium salt
        ii) glycerine
        iii) triethyleneglycol diamine
        iv) $H_2NCH_2(CH_3)CHCH_2CH_2CH_2NH_2$
        v) $N(CH_2CH_2NH_2)_3$
    b) a glycerine-immiscible oil component comprising
        vi) mineral oil
        vii) $OCN(C_6H_{10})CH_2(C_6H_{10})NCO$
        viii) a surfactant;
    wherein each of ingredients iii), iv) and v) are present at mole equivalent ratios of primary amine to isocyanate of about 0.2–0.5:1;
    said admixing being conducted under conditions effective to form an polar liquid-in-oil emulsion, wherein said polar component is dispersed in the form of microscopic emulsion droplets in a glycerine-immiscible oil component continuous phase, and thereby surrounding each of said droplets with a solid capsule wall.

3. The method of claim 2, wherein the mole equivalent ratio of total primary amine functionality to isocyanate functionality is about 0.8:1 to 1:1.2.

4. The method of claim 2, wherein the mole equivalent ratio of total primary amine functionality to isocyanate functionality is about 1:1.1.

5. Microcapsules made by the method of claim 1.

6. The method of claim 1, wherein the aliphatic polyisocyanate comprises cycloalkyl moieties.

7. The method of claim 1, wherein the aliphatic polyisocyanate contains 5–30 carbons.

8. The method of claim 1, wherein the aliphatic polyisocyanate contains two isocyanate functionalities.

9. The method of claim 1, wherein the aliphatic polyisocyanate contains three isocyanate functionalities.

10. The method of claim 1, wherein the aliphatic polyisocyanate is selected from the group consisting of dicyclohexylmethane-4,4'-diisocyanate; hexamethylene 1,6-diisocyanate; isophorone diisocyanate; trimethylhexamethylene diisocyanate; trimer of hexamethylene 1,6-diisocyanate; trimer of isophorone diisocyanate; 1,4-cyclohexane diisocyanate; 1,4-(dimethylisocyanato) cyclohexane; biuret of hexamethylene diisocyanate; urea of hexamethylene diisocyanate; trimethylenediisocyanate; propylene-1,2-diisocyanate; and butylene-1,2-diisocyanate.

11. The method of claim 1, wherein the quaternary ammonium salt is an antimicrobial quaternary ammonium salt.

12. The method of claim 1, wherein the quaternary ammonium salt is alkyl dimethyl benzyl chloride, dialkyl dimethyl ammonium chloride, methylbenzethonium chloride, chlorhexidine gluconate, stearyl dimethyl benzyl ammonium chloride, cetyl trimethyl ammonium chloride and dicetyl dimethyl ammonium chloride, alkyl imidaxolinium methosulfate and mixtures thereof.

13. The method of claim 1, wherein the quaternary ammonium salt comprises at least about 5% by weight of the microcapsule.

14. The method of claim 1, wherein the mole equivalent ratio of total amine functionality to isocyanate functionality is about 0.8:1 to 1:1.2.

15. The method of claim 1, wherein the mole equivalent ratio of total amine functionality to isocyanate functionality is about 1:1.1.

16. Microcapsules made by the method of claim 2.

* * * * *